United States Patent [19]

Rasmussen

[11] 4,402,964

[45] Sep. 6, 1983

[54] N-ARYL-N'-(3-METHYL OR ETHYL-4-OXO-THIAZOLIDINYLIDENE)UREAS USEFUL FOR THE TREATMENT OF EPILEPSY

[75] Inventor: Chris R. Rasmussen, Ambler, Pa.

[73] Assignee: McNeilab, Inc., Spring House, Pa.

[21] Appl. No.: 321,669

[22] Filed: Nov. 16, 1981

[51] Int. Cl.³ .................. A61K 31/425; C07D 277/14
[52] U.S. Cl. .................................... 424/270; 548/185
[58] Field of Search ......................... 548/185; 424/270

[56] References Cited

U.S. PATENT DOCUMENTS 3,297,708  1/1967  Garber et al. .................. 424/270
3,637,725  1/1972  Werbel .......................... 424/270 X

OTHER PUBLICATIONS

Kretov, et al., Zh. Obshch. Khim., 34(10), pp. 3365–3367 (1964).
Prelica, et al., Polish J. Pharmacol. Pharm. 25(2), 163–170 (1973).
Martin, et al., Chemical Abstracts, vol. 71, 91056c (1969).

Primary Examiner—Donald G. Daus
Assistant Examiner—Diana G. Rivers

[57] ABSTRACT

N-aryl-N'-(3-methyl or ethyl-4-oxo-thiazolidinylidene)urea compounds of Formula I

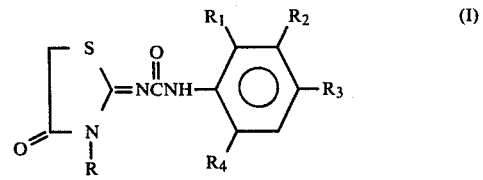

wherein:
R is $CH_3$, $C_2H_5$;
$R_1$ is chosen from F, Cl, Br, $CH_3$, $C_2H_5$, $OCH_3$ and $CF_3$;
$R_2$ is H or $CH_3$;
$R_3$ is H or F;
$R_4$ is chosen from F, Cl, Br, $CH_3$, $C_2H_5$, $OCH_3$ and $CF_3$;

have anticonvulsant activity and are useful in the treatment of epilepsy.

15 Claims, No Drawings

N-ARYL-N'-(3-METHYL OR ETHYL-4-OXOTHIAZOLIDINYLIDENE)UREAS USEFUL FOR THE TREATMENT OF EPILEPSY

FIELD OF THE INVENTION

This invention relates to novel compounds, which are N-aryl-N'-(3-methyl- or ethyl-4-oxothiazolidinylidene) ureas, shown in Formula I; to pharmaceutical compositions containing said compounds in a pharmaceutically acceptable carrier; and to a process for treating mammals having symptoms of epilepsy by administering thereto said pharmaceutical compositions.

DESCRIPTION OF THE PRIOR ART

A compound, differing from one of those of the present invention in lacking the 3-methyl or ethyl substituent on the N-atom of the oxothiazolidinylidene radical is known. Its structure is:

(Ia)

where $R_1$, $R_2$, $R_3$ and $R_4$ are all H. It is disclosed in two journal articles: (1) A. E. Kretov and A. S. Bespalyi, *Zh. Obshch. Khim.* 34, 3406 (1964) (English translation); and (2) D. Prelicz, E. Kleczek, and H. Siaglo, *Polish J. Pharmacol. and Phar.* 25, 163 (1973).

Said journal articles do not teach any biological activity for said prior art compound; and furthermore, it was not active when tested in the Maximal Electroshock (MES) test at 200 mg/kg, p.o. which test is used to show the anticonvulsant utility of the compounds of the present invention.

SUMMARY OF THE INVENTION

The present invention is directed to N-aryl-N'-(3-methyl- or ethyl-4-oxothiazolidinylidene) urea compounds having the structure of Formula I below:

(I)

wherein
- R is $CH_3$ or $C_2H_5$;
- $R_1$ is chosen from F, Cl, Br, $CH_3$, $C_2H_5$, $OCH_3$ and $CF_3$;
- $R_2$ is H or $CH_3$;
- $R_3$ is H or F;
- $R_4$ is chosen from F, Cl, Br, $CH_3$, $C_2H_5$, $OCH_3$ and $CF_3$.

A preferred group of compounds for purposes of the present invention, are those of Formula I above wherein
- R is $CH_3$;
- $R_1$ remains as defined above;
- $R_2$ and $R_3$ are each H;
- $R_4$ remains as defined above.

The compounds of Formula I are active in the Maximal Electroshock (MES) test, which indicates anticonvulsant activity, and that such compounds are useful for the treatment of epilepsy. Thus the present invention also relates to a process for treating epilepsy by administering to an animal in need of such treatment a pharmaceutical composition containing a therapeutically sufficient amount of said compound of Formula I and a carrier; and to the aforesaid pharmaceutical composition.

The compounds of the present invention can be prepared by the following reaction scheme:

(II)        (III)

The starting materials II are 2-imino-3-methyl- or ethyl-thiazolidin-4-ones. They are known in the literature, and are also called pseudothiohydantoins. Many of the substituted phenyl isocyanates III are known in the literature also, and any which are not can be prepared by the standard procedures well-known in the art of preparation of such type compounds.

The reaction is carried out in a dry solvent. Useful solvents include: benzene, toluene, xylene and the like (aromatic hydrocarbons), DMF, DMSO, 1-methyl-2-pyrrolidinone, hexamethylphosphoric acid triamide (HMPA), sulfolane and the like (polar aprotic solvents) and THF, dioxane, acetonitrile, acetone, 2-butanone and the like.

These reactions may be conveniently carried out from ambient temperatures to about 100° C.

Equimolar ratios of reactants II and III are used, although a slight stoichiometric excess of II is permissible.

The reaction products I may be purified by standard techniques known in the art, e.g., recrystallization.

The compounds of Formula I have been found to have useful pharmacological properties as demonstrated by the Maximal Electroshock (MES) test.

Activity in the MES test, indicating anticonvulsant activity, is characterized by a block of the tonic extensor seizure caused by applying an electric shock to mice via corneal electrodes as described in Swinyard et al., *J. Pharmacol. Exp. Ther.,* 106, 319–330 (1952) and recorded as % block. A more recent description of current practice in anticonvulsant drug screening has also been reported by Swinyard et al., *Epilepsia,* 19, 409–428 (1978).

The results obtained in the MES test are as set forth in Table I:

TABLE I $$\text{(I)}$$

| Ex. No. | McN No. | R | R₁ | R₂ | R₃ | R₄ | Mice MES test results dose (mg/kg p.o.) |
|---|---|---|---|---|---|---|---|
| I | 4249 | Me | Me | H | H | Me | ED₅₀(9.96) |
| II | 4248 | Me | Cl | H | H | Cl | ED₅₀(28.3) |
| III | 4625 | Me | Me | H | H | Et | Active (10)[1] |
| IV | 4630 | Me | Cl | H | H | Me | ED₅₀(28.54) |
| V | 4652 | Me | Et | H | H | Et | ED₅₀(17.5) |
| VI | 4672 | Me | Br | H | F | Br | Active (200)[2] |
| VII | 4738 | Me | Br | H | H | Br | ED₅₀(83.9) |
| VIII | 4679 | Me | Me | Me | H | H | ED₅₀(127.9) |
| IX | 4748 | Me | OMe | H | H | OMe | ED₅₀(35.7) |
| X | 4764 | Me | F | H | H | F | ED₅₀(52.23) |

[1] 10% block at 10 mg/kg - only dose available
[2] 60% block at 200 mg/kg

In said table, the ED₅₀ result means that 50% of the animals show a block of tonic extensor convulsions in the MES test.

Table II contrasts results obtained with the prior art compound and two related compounds of Formula Ia:

TABLE II $$\text{(Ia)}$$

| McN No. | R₁ | R₂ | R₃ | R₄ | Mice MES test results dose (mg/kg p.o.) |
|---|---|---|---|---|---|
| 1. X-888 | H | H | H | H | IA (200) |
| 2. 4241 | Me | H | H | Me | ED₅₀(241.5) (range 196.5-296.9) |
| 3. 4242 | Cl | H | H | Cl | IA (200) |

IA = inactive

As is evident by comparing the results shown in Table I to those in Table II, the compounds of Examples I and II of the present invention are from more than 10 to 24 times more potent anticonvulsants than their prior art-related counterparts (McN-4241, 4242 of Table II).

For treating epilepsy, the compounds of Formula I may be employed at a daily dosage range of from 30 to 2000 mg usually in 2-4 divided doses. A unit dose is expected to contain from about 10–500 milligrams of the active ingredient.

To prepare the pharmaceutical compositions of this invention, an N-aryl-N'-(3-methyl or ethyl-4-oxo-thiazolidinylidene) urea compound of Formula 1, as the active ingredient, is intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful, suppository and the like, from about 10 to about 500 mg of the active ingredient.

The foregoing compositions are particularly suitable for use in the treatment of epilepsy or the symptoms of epilepsy by a method comprising internally administering to a subject suffering from the symptoms of epilepsy compositions comprising an effective epilepsy inhibiting amount of a compound of Formula I.

The following examples illustrate the invention but are not to be construed as limiting.

EXAMPLE I

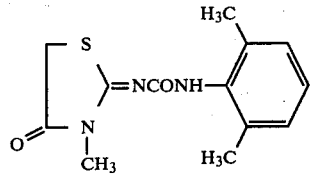

N—(2,6-dimethylphenyl)-N'—(3-methyl-4-oxo-2-thiazolidinylidene)urea - McN-4249

A solution of 6.0 g (0.040 mole) of 2,6-dimethylphenyl isocyanate in 20 ml of dry DMF was added dropwise to a solution of 5.2 g (0.040 mole) of 2-imino-3-methylthiazolidin-4-one in 60 ml of dry DMF. The reaction mixture was stirred at room temperature for four hours, filtered from small amounts of insolubles, poured into water, and the crude product was filtered. Two recrystallizations from DMF-H₂O gave 8.3 g (75%) of pure product; m.p. 179°–181° C.

Calc'd for $C_{13}H_{15}N_3O_2S$: C, 56.30; H, 5.45; N, 15.15;
Found: C, 56.36; H, 5.46; N, 15.17;
UV Max (MeCN): 238 (ε23,000); 256 nm (ε17,300)
IR(KBr): 3350; 2970, 2920, 2230; 1715; 1658 cm⁻¹
NMR(DMSO-d₆): δ 9.30 (s, 1H,NH); 7.13 (s, 3H, aromatic) 3.92 (s, 2H, SCH₂CO); 3.25 (s, 3H, NCH₃); 2.28 (s, 6H, 2CH₃)

EXAMPLE II

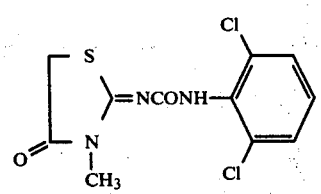

N—(2,6-dichlorophenyl)-N'—(3-methyl-4-oxo-2-thiazoli-dinylidene)urea - McN-4248

A solution of 7.5 g (0.040 mole) of 2,6-dichlorophenylisocyanate in 30 ml of dry benzene (filtered from some insolubles) was added dropwise to a solution of 5.2 g (0.040 mole) of 2-imino-3-methyl thiazolidin-4-one in 100 ml of dry DMF. The reaction mixture was stirred at room temperature for 4 hours, evaporated in vacuo at room temperature to remove benzene then poured into water, and the solid filtered. Two recrystallizations from DMF-H$_2$O gave 8.5 g (67%) of pure product; m.p. 160°-162° C.

Calc'd for C$_{11}$H$_9$Cl$_2$N$_3$O$_2$S: C, 41.52; H, 2.85; N, 13.21; Found: C, 41.57; H, 2.88; N, 13.21

UV MAX (MeCN): 228 ($\epsilon$20,600); 242 ($\epsilon$25,000); 258 nm ($\epsilon$18,200).

IR(KBr): 3370; 3070; 2920; 2840; 1735; 1722; 1650 cm$^{-1}$

NMR(DMSO-d$_6$): $\delta$ 9.80 (s, 1H,NH); 7.79- 7.20 (m, 3H, aromatic); 3.90 (s, 2H, S—CH$_2$CO); 3.25 (s, 3H, N—CH$_3$)

EXAMPLE III

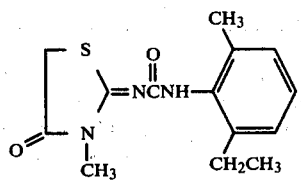

N—(2-ethyl-6-methylphenyl-N'—(3-methyl-4-oxo-2-thiazolidinylidene)urea-McN-4645

A 6.51 g (50 mmole) sample of 2-imino-3-methyl-thiazolidin-4-one was dissolved in 150 ml of dry toluene with heating.

This solution was filtered into a 500 ml erlenmeyer flask filled with argon. Then 8.06 g (50 mmole) of 2-ethyl-6-methylphenylisocyanate was dissolved in 20 ml of pentane and filtered into the stirring thiazolidinone solution while still warm. The reaction solution was stirred at room temperature in a stoppered reaction vessel. The mixture was cooled in ice after stirring for 40 hours and 10.33 g of white solid was filtered, m.p. 118°-122° C. A second crop of 0.9 g was recovered after 100 ml of heptane was added to the filtrate. The combined crops were recrystallized from 50 ml of toluene to give 9.4 g of white fluffy solid, m.p. 119.5°-121° C. This solid was recrystallized from methylene chloride/methyl cyclohexane to give 8.7 g (60%) of pure white crystals, m.p. 120°-121.5° C. One additional recrystallization from DMF/H$_2$O gave 7.8 g (53.5%) of analytically pure white crystals, m.p. 120°-121° C. (corr.)

Anal. Calc'd for C$_{14}$H$_{17}$N$_3$O$_2$S (291.367): C, 57.71; H, 5.88; N, 14.42. Found: C, 57.65; H, 5.92; N, 14.44; UV Max (MeOH): 238 ($\epsilon$23,100) and 258 nm ($\epsilon$16,400)

EXAMPLE IV

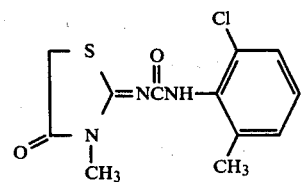

N—(2-chloro-6-methylphenyl)-N'—(3-methyl-4-oxo-2-thiazolidinylidene)urea - McN-4630

6.51 g (50 mmole) of 2-imino-3-methylthiazolidin-4-one was dissolved in 150 of dry toluene with heating. The hot solution was filtered into the reaction vessel under an N$_2$ stream and stirred under N$_2$ (CaCl$_2$ drying tube). 8.38 g (50 mmoles) of 2-chloro-6-methylphenylisocyanate was dissolved in 20 ml of pentane and the entire solution was added all at once to the stirring thiazolidinone. The reaction was stirred at room temperature for 5.5 hours. 100 ml of heptane was added to the reaction causing crystal formation. The solution was stirred for 25 minutes before filtering 10.7 g (72%) of yellow solid. The filtrate was cooled in ice and gave 1.95 g of a second crop. The combined crops were recrystallized from toluene giving 11.66 g of yellow solid, m.p. 124.5°-133° C. This solid was recrystallized from toluene (charcoal) by adding heptane to the clound point, affording 7.73 g of pale yellow solid, m.p. 131°-132.5° C. A second crop of 2.73 g was obtained from the ice cooled filtrate. The combined crops were dissolved in 50 ml of methylene chloride, charcoaled, and filtered through diatomaceous earth. Methylcyclohexane was added as the methylene chloride was evaporated on a steambath until the solution became cloudy. Seeding gave 9.45 g (63.5%) of pure white crystals; m.p. 132.5°-133° C. (corr.).

Anal. Calc'd for C$_{12}$H$_{12}$ClN$_3$O$_2$S (297.759): C, 48.41; H, 4.06; N, 14.11; Found: C, 48.29; H, 4.08; N, 14.11

UV Max (MeOH): 239 ($\epsilon$23,900) and 256 nm ($\epsilon$17,500) nm

EXAMPLES V-X

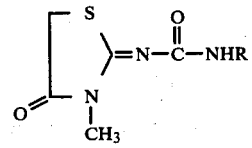

2-Thiazolidin-4-one Ureas - A General Method

Following the teaching of Example II, a solution of 6.51 g (0.05 mole) of 2-imino-3-methylthiazolidin-4-one in 150 to 200 mls of warm toluene was treated with charcoal and filtered through diatomaceous earth. The warm filtrate was immediately treated with a solution of 0.05 mole of the appropriate substituted phenylisocyanate in about 30 mls of toluene, stoppered and stirred for about 24 hours at ambient temperatures, filtered, and recrystallized to yield the corresponding ureas listed in Table III.

TABLE III

| Ex. No. | R | Empirical Formula | % Yield | m.p. (°C.) | Recryst. Solv. | UV Max. (MeOH) nm (ε) | ANAL. Calc'd C | H | N | Found C | H | N | McN. No. |
|---|---|---|---|---|---|---|---|---|---|---|---|---|---|
| V | 2,6-Et$_2$Ph | C$_{15}$H$_{19}$N$_3$O$_2$S | 88.4 | 119–121 | MC/MCH | 238(23.2K) 257(Shl)(16.3K) | 58.99 | 6.27 | 13.76 | 59.04 | 6.30 | 13.80 | 4652 |
| VI | 2,6-Br$_2$—4-FPh | C$_{11}$H$_8$Br$_2$FN$_3$O$_2$S | 64.3 | 126.5–128 | MC/MCH | 236.5(26.5K) 260(Shl)(16.5K) | 31.08 | 1.90 | 9.88 | 31.08 | 1.91 | 9.86 | 4672 |
| VII | 2.6-Br$_2$Ph | C$_{11}$H$_9$Br$_2$N$_3$O$_2$S | 59.9 | 162.5–164 | MC/MCH | 236(25.7K) 260(Shl)(16.9K) | 32.46 | 2.23 | 10.32 | 32.48 | 2.25 | 10.33 | 4738 |
| VIII | 2,3-Me$_2$Ph | C$_{13}$H$_{15}$N$_3$O$_2$S | 86.0 | 183–184 | MC/T | 237(20.6K) 262(15.9K) | 56.30 | 5.45 | 15.15 | 56.32 | 5.48 | 15.12 | 4679 |
| IX | 2,6-DiOMePh | C$_{13}$H$_{15}$N$_3$O$_4$S | 39 | 153–155 | MC/E | 236(21.4K) 261(15.2K) | 50.48 | 4.89 | 13.58 | 50.53 | 4.90 | 13.56 | 4748 |
| X | 2,6-DiFPh | C$_{11}$H$_9$F$_2$N$_3$O$_2$S | 21 | 167–168 | T | 242(24.4K) 260(18.1K) | 46.31 | 3.18 | 14.73 | 46.62 | 3.42 | 14.52 | 4764 |

K = 1,000

EXAMPLE XI

By following the teachings of either Example I or II, but substituting the specific 2,6-disubstituted phenyl isocyanate of said example with an equimolar amount of the appropriate 2,6-disubstituted phenyl isocyanate, the following ureas of Formula I can be produced:

N-(2-chloro-6-trifluoromethyl)phenyl-N'-(3-methyl-4-oxo-2-thiazolidinylidene)urea.

N-(2-methyl-6-trifluoromethyl)phenyl-N'-(3-methyl-4-oxo-2-thiazolidinylidene)urea.

N-(2-methoxy-6-trifluoromethyl)phenyl-N'-(3-methyl-4-oxo-2-thiazolidinylidene(urea).

N-(2-bromo-6-trifluoromethyl)phenyl-N'-(3-methyl-4-oxo-2-thiazolidinylidene)urea.

N-(2,6-bis-trifluoromethyl)phenyl-N'-(3-methyl-4-oxo-2-thiazolidinylidene)urea.

N-(2-chloro-6-fluoro)phenyl-N'-(3-methyl-4-oxo-2-thiazolidinylidene)urea.

N-(2-bromo-6-chloro)phenyl-N'-(3-methyl-4-oxo-2-thiazolidinylidene)urea.

N-(2-methyl-6-methoxy)-phenyl-N'-(3-methyl-4-oxo-2-thiazolidinylidene)urea.

N-(2-chloro-6-methoxy)phenyl-N'-(3-methyl-4-oxo-2-thiazolidinylidene)urea.

EXAMPLE XII

By following the teachings of Example I, but replacing the 2-imino-3-methylthiazolidin-4-one with an equimolar amount of 2-imino-3-ethylthiazolidin-4-one followed by treatment with an equimolar amount of an appropriate 2,6-disubstituted phenyl isocyanate, the following ureas of Formula I can be produced:

N-(2,6-dimethyl)phenyl-N'-(3-ethyl-4-oxo-2-thiazolidinylidene)urea.

N-(2-chloro-6-methyl)phenyl-N'-(3-ethyl-4-oxo-2-thiazolidinylidene)urea.

N-(2,6-dichloro)phenyl-N'-(3-ethyl-4-oxo-2-thiazolidinylidene)urea.

N-(2,6-dimethoxy)phenyl-N'-(3-ethyl-4-oxo-2-thiazolidinylidene)urea.

N-(2-methoxy-6-methyl)phenyl-N'-(3-ethyl-4-oxo-2-thiazolidinylidene)urea.

N-(2-chloro-6-fluoro)phenyl-N'-(3-ethyl-4-oxo-2-thiazolidinylidene)urea.

N-(2-ethyl-6-methyl)phenyl-N'-(3-ethyl-4-oxo-2-thiazolidinylidene)urea.

N-(2-methyl-6-trifluoromethyl)phenyl-N'-(3-ethyl-4-oxo-2-thiazolidinylidene)urea.

N-(2-chloro-6-trifluoromethyl)phenyl-N'-(3-ethyl-4-oxo-2-thiazolidinylidene)urea.

N-(2-methoxy-6-trifluoromethyl)phenyl-N'-(3-ethyl-4-oxo-2-thiazolidinylidene)urea.

N-(2,6-bis-trifluoromethyl)phenyl-N'-(3-ethyl-4-oxo-2-thiazolidinylidene)urea.

N-(2,6-dibromo)phenyl-N'-(3-ethyl-4-oxo-2-thiazolidinylidene)urea.

EXAMPLE XIII

One thousand (1,000) hard gelatin capsules, each containing 200 milligrams of active ingredient, which is N-(2,6-dimethylphenyl)-N'-(3-methyl-4-oxo-2-thiazolidinylidene)urea or alternatively the compound of any previous example can be prepared from the following formulation:

|  | Grams |
|---|---|
| Active ingredient | 200 |
| Starch | 100 |
| Lactose | 150 |
| Talc | 50 |
| Calcium stearate | 5 |

A uniform mixture of the ingredients can be prepared by blending and employed to fill two-piece hard gelatin capsules. The capsules are suitable to be orally administered to subjects with symptoms of epilepsy.

EXAMPLE XIV

Gelatin capsules can be prepared as described in Example XIII except that in the formulation, 400 grams of N-(2,6-dichlorophenyl)-N'-(3-methyl-4-oxo-2-thiazolidinylidene)urea as active agent providing capsules containing 400 milligrams of said active agent.

EXAMPLE XV

One thousand (1,000) compressed tablets, each containing 500 milligrams of N-(2-chloro-6-methylphenyl)-N'-(3-methyl-4-oxo-2-thiazolidinylidene)urea as the active ingredient can be prepared from the following formulation:

|  | Grams |
|---|---|
| Active ingredient | 500 |
| Starch | 75 |
| Microcrystalline cellulose | 100 |
| Calcium stearate | 5 |

The finely powdered ingredients are to be mixed well and granulated with 10 percent starch paste. The granulation is to be dried and compressed into tablets using starch as a disintegrant and calcium stearate as a lubricant.

EXAMPLE XVI

Parenteral formulations, for intramuscular injection can be prepared as follows:

One thousand (1,000) 1 ml vials, each containing 50 milligrams of active ingredient, which is N-(2,6-dimethylphenyl)-N'-(3-methyl-4-oxo-2-thiazolidinylidene)urea can be prepared from the following formulation:

|  | Quantity |
| --- | --- |
| Active ingredient | 50 grams |
| Benzyl alcohol | 9 grams |
| Povidone | 20 grams |
| Water for injection, q.s. | 1000 ml |

EXAMPLE XVII

One thousand (1,000) 2 gram cocoa butter suppositories, each containing 200 milligrams of active ingredient, which is N-(2,6-dimethylphenyl)-N'-(3-methyl-4-oxo-2-thiazolidinylidene)urea can be prepared from the following formulation:

|  | Quantity |
| --- | --- |
| Active ingredient | 200 grams |
| Cocoa butter | 1800 grams |

I claim:

1. An N-aryl-N'-(1-methyl or ethyl)-4-oxo-thiazolidinylidene)urea derivative having the formula

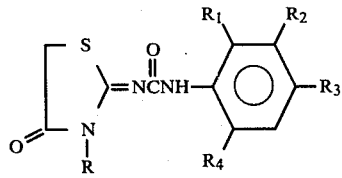

wherein

R is $CH_3$ or $C_2H_5$;

$R_1$ is chosen from F, Cl, Br, $CH_3$, $C_2H_5$, $OCH_3$ and $CF_3$;

$R_2$ is H or $CH_3$;

$R_3$ is H or F;

$R_4$ is chosen from F, Cl, Br, $CH_3$, $C_2H_5$, $OCH_3$ and $CF_3$.

2. A compound of claim 1 wherein in the formula

R is $CH_3$;

$R_1$ is F, Cl, Br, $CH_3$, $C_2H_5$, $OCH_3$ and $CF_3$;

$R_2$ is H;

$R_3$ is H;

$R_4$ is F, Cl, Br, $CH_3$, $C_2H_5$, $OCH_3$ and $CF_3$.

3. A compound of claim 1 which is N-(2,6-dimethylphenyl)-N'-(3-methyl-4-oxo-2-thiazolidinylidene)urea.

4. A compound of claim 1 which is N-(2,6-dichlorophenyl)-N'-(3-methyl-4-oxo-2-thiazolidinylidene)urea.

5. A compound of claim 1 which is N-(2-ethyl-6-methylphenyl)-N-'-(3-methyl-4-oxo-2-thiazolidinylidene)urea.

6. A compound of claim 1 which is N-(2-chloro-6-methylphenyl)-N'-(3methyl-4-oxo-2-thiazolidinylidene)urea.

7. A compound of claim 1 which is N-(2,6-diethylphenyl)-N'-(3-methyl-4-oxo-2-thiazolidinylidene)urea.

8. A compound of claim 1 which is N-(2,6-dibromophenyl)-N'-(3-methyl-4-oxo-2-thiazolidinylidene)urea.

9. A compound of claim 1 which is N-(2,6-dimethoxyphenyl)-N'-(3-methyl-4-oxo-2-thiazolidinylidene)urea.

10. A compound of claim 1 which is N-(2,6-difluorophenyl)-N'-(3-methyl-4-oxo-2-thiazolidinylidene)urea.

11. A pharmaceutical composition useful for the treatment of the symptoms of epilepsy comprising as the active ingredient, a compound of claim 1, together with a pharmaceutically acceptable carrier.

12. A pharmaceutical composition according to claim 1, wherein the active ingredient is a compound of claim 2.

13. A pharmaceutical composition according to claim 12 wherein the active ingredient is present in a unit dosage amount of 10–500 milligrams.

14. A method of treating the symptoms of epilepsy in a mammal requiring such treatment by internally administering thereto a pharmaceutical composition of claim 13 in an effective epilepsy-inhibiting amount.

15. A method according to claim 14 wherein the pharmaceutical composition is administered at a daily dosage range of 30 to 200 mg.

* * * * *